US00PP27492P2

(12) United States Plant Patent
Delabroye

(10) Patent No.: US PP27,492 P2
(45) Date of Patent: Dec. 20, 2016

(54) ***HEUCHERA* PLANT NAMED 'GAUGUIN'**

(50) Latin Name: ***Heuchera* hybrid**
Varietal Denomination: Gauguin

(71) Applicant: Thierry Delabroye, Hantay (FR)

(72) Inventor: Thierry Delabroye, Hantay (FR)

(73) Assignee: Sandrine Delabroye, Hantay (FR)

( * ) Notice: Subject to any disclaimer, the term of this patent is extended or adjusted under 35 U.S.C. 154(b) by 76 days.

(21) Appl. No.: 14/121,866

(22) Filed: Oct. 28, 2014

(51) Int. Cl.
*A01H 5/12* (2006.01)

(52) U.S. Cl.
USPC ..... Plt./440

(58) Field of Classification Search
USPC ..... Plt./440
See application file for complete search history.

(56) References Cited

PUBLICATIONS

Bloembollen isie *Heuchera* series Master Painters at Plantarium Aug. 16, 2012, retrieved on Mar. 23, 2016, retrieved from the Internet at <http://www.bloembollenvisie.nl/Nieuws/Paginas/HeucheraserieMasterPainters%E2%84%A2opPlantarium.aspx#.VvKD6vlVgnE> 2 pp.*
Bloembollen isis Google English translation 1 page.*

* cited by examiner

*Primary Examiner* — June Hwu
(74) *Attorney, Agent, or Firm* — Penny J. Aguirre

(57) ABSTRACT

A new cultivar of hybrid *Heuchera* named 'Gauguin', that is characterized by its compact plant habit with a tight mound of foliage, its leaves that are dark brown-red in color with narrow margins colored yellow-green, its moderate amount of flowering stems, and its light reddish-pink flowers on dark brownish-red flowering stems.

2 Drawing Sheets

Botanical classification: *Heuchera* hybrid.
Cultivar designation: 'Gauguin'.

BACKGROUND OF THE INVENTION

The present invention relates to a new and distinct cultivar of *Heuchera* of hybrid origin, botanically known as a *Heuchera* and is hereinafter referred to by its cultivar name 'Gauguin'.

The new cultivar was discovered as a chance seedling in a trial field by the Inventor in Hantay, France in June of 2010. The trial field contained hundreds of cultivars and proprietary seedlings of *Heuchera* from the Inventor's breeding program. The exact parentage of 'Gauguin' is therefore unknown.

Asexual propagation of the new cultivar was first accomplished under the direction of the Inventor by in vitro propagation initiated from meristem tissue in Rijswijk, The Netherlands in October of 2012. Asexual propagation of the new cultivar by in vitro propagation and stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Gauguin' as a new and unique cultivar of *Heuchera*.

1. 'Gauguin' exhibits a compact plant habit with a tight mound of foliage.
2. 'Gauguin' exhibits leaves that are dark brown-red in color with narrow margins colored yellow-green.

3. 'Gauguin' exhibits a moderate amount of flowering stems.
4. 'Gauguin' exhibits light reddish-pink flowers on dark brownish-red flowering stems.

'Gauguin' can be most closely compared to the *Heuchera* cultivars 'Caramel' (U.S. Plant Pat. No. 16,560) and 'Vulcano' (U.S. Plant Pat. No. 25,625). Both are similar to 'Gauguin' in foliage coloration. 'Caramel' differs from 'Gauguin' in having smaller leaves that are slightly lighter in color with margins that are more deeply lobed, and in rarely producing flowering stems. 'Vulcano' differs from 'Gauguin' in having a taller plant habit, in having leaves that are lighter in color with more conspicuous veins, and in having flowers that are deep pink in color.

BRIEF DESCRIPTION OF THE DRAWINGS

The accompanying colored photographs illustrate the overall appearance and distinct characteristics of the new *Heuchera*. The photographs were taken of a plant three-years in age as grown outdoors in 23-cm containers in Hillegom, The Netherlands.

The photograph in FIG. 1 provides a side view of the plant habit of 'Gauguin' in bloom.

Figure 1:
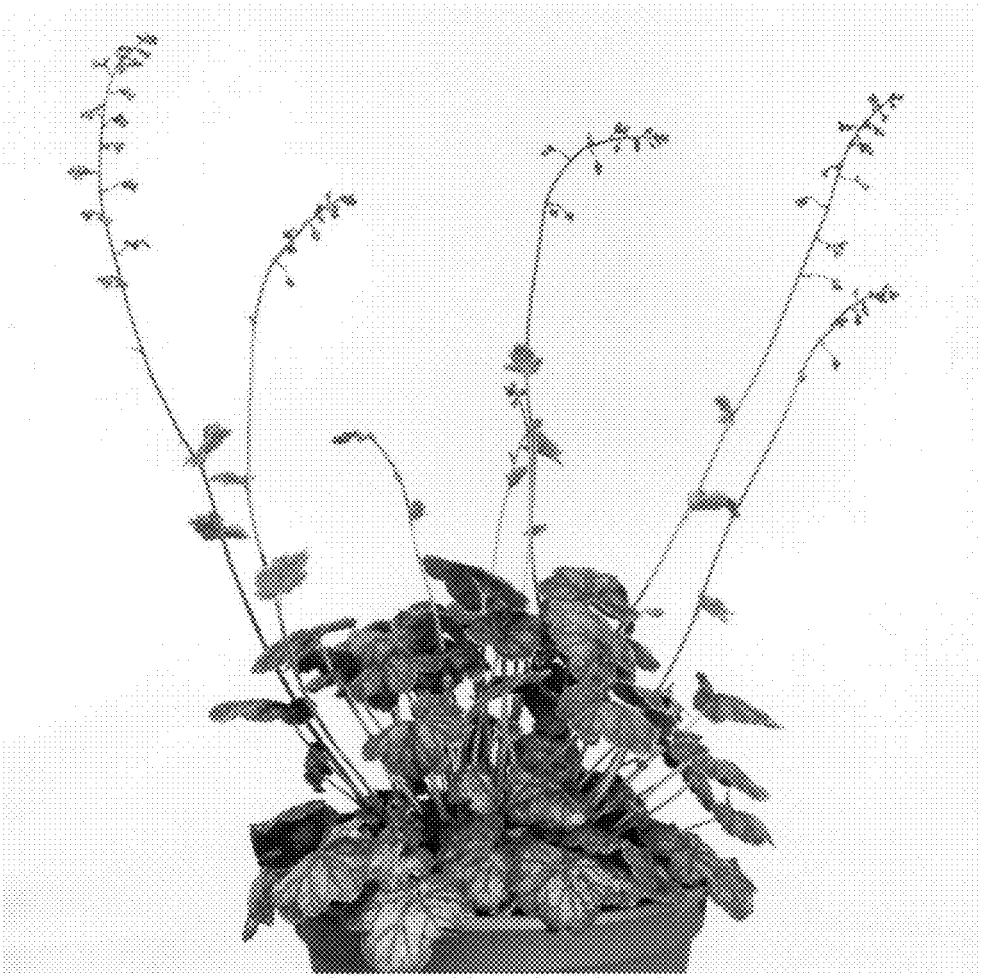
Figure 2:
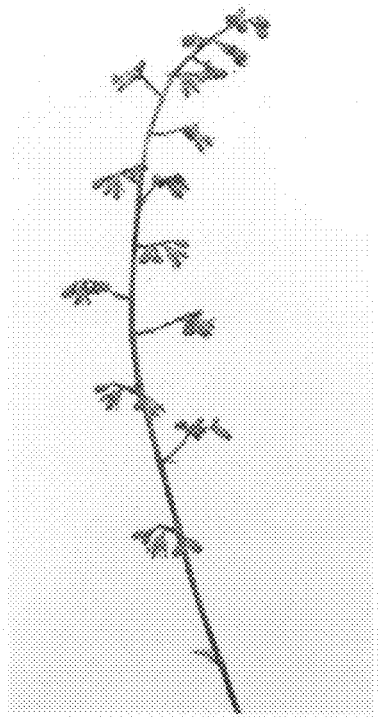

The photograph in FIG. 2 provides a close-up view of the inflorescences of 'Gauguin'.

Figure 3:
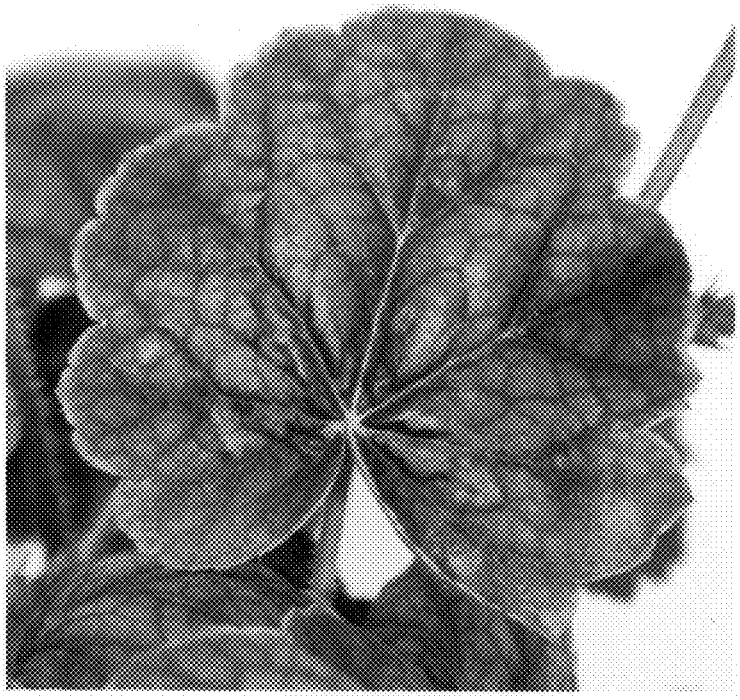

The photograph in FIG. 3 provides a close-up view of the foliage of 'Gauguin'.

The colors in the photographs are as close as possible with the digital photography techniques available, the color values cited in the detailed botanical description accurately describe the colors of the new *Heuchera*.

DETAILED BOTANICAL DESCRIPTION OF THE PLANT

The following is a detailed description of three-year old plants of the new cultivar as grown outdoors in Hillegom, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—An average of 4 weeks from late spring into summer in The Netherlands.

*Plant type.*—Herbaceous perennial.

*Plant habit.*—Compact plant habit with a tight mound of foliage.

*Height and spread.*—An average of 50 cm in height (including inflorescences) and 55 cm in width on a three year-old plant.

*Hardiness.*—At least in U.S.D.A. Zones 3 to 9.

*Diseases and pests.*—Not more susceptible to pests and diseases than other *Heuchera* cultivars.

*Root description.*—Fibrous roots on woody rootstalks.

*Propagation.*—In vitro propagation and stem cuttings.

*Growth rate.*—Moderate.

Stem description (peduncle, flowering stem):

*Shape.*—Round.

*Stem color.*—183A to 183B with base 177B to 177C.

*Stem size.*—Primary; an average of 2 mm in diameter and 55.1 cm in length (16.4 cm from base to the apex of inflorescence, secondary; an average of 0.75 mm in diameter and 1.7 cm in length.

*Stem strength.*—Moderate.

*Stem aspect.*—Average angle of primary peduncle; 80° (horizontal=0°), average angle of secondary peduncles; 85° to primary peduncle (=0°).

*Stem surface.*—Densely covered with very short hairs, an average of 1 mm in length, NN155D in color.

*Stem number.*—Average of 20 flowering stems.

*Branching habit.*—Flowering stems emerge from basal rosette.

Foliage description:

*Leaf shape.*—Broad ovate, seven lobed, middle lobe is longer than lateral lobes.

*Leaf division.*—Simple.

*Leaf base.*—Hastate, lobes free.

*Leaf apex.*—Acute.

*Leaf venation.*—Laciniate, color; upper surface 150C to 150D with tertiary veins 200A and lower surface 144D, lower surface main and secondary veins moderately covered with very short hairs an average of 0.5 mm in length and N155B to N155D in color.

*Leaf margins.*—Lobed with average of 7 lobes per leaf, very shallow lobe depth, lobe margins crenate and very weakly undulate, moderately covered with very short hairs an average of 0.5 mm in length and N155B to N155D in color.

*Leaf attachment.*—Petiolate.

*Leaf arrangement.*—Alternate in basal rosettes.

*Leaf orientation.*—Typically nearly perpendicular to petiole and slightly cupped down.

*Leaf surface.*—Upper surface; dull, velvety, occasionally glaucescent, and moderately covered with very short hairs an average of 0.5 mm in length and N155B to N155D in color, lower surface; moderately glossy.

*Leaf color.*—In the spring and early summer, young leaves upper surface; 166A to 166B with narrow margins N144A to N144B and lower surface; 176B with narrow margins 144B, mature and fall leaves upper surface; 166A with very narrow margins N144B, mature and fall leaves lower surface; a blend between 176B and 177A with very narrow margins 162A, color darkens to primarily 177A in the late summer and fall.

*Leaf size.*—An average of 10.4 cm in length and 9.3 cm in width.

*Leaf quantity.*—An average of 13 per basal rosette.

*Petioles.*—An average of 17.3 cm in length and 3 mm in diameter, color; 144C strongly suffused with 176A to 176B, especially towards the base, surface; densely covered with very short soft hairs an average of 1 mm in length and NN155D in color.

*Stipules.*—Small leafy stipules at the base of each leaf, narrow acute apex, an average of 1.7 cm in length and 2.5 mm in width, color; NN155C with apex 145C to 145D.

Flower description:

*Inflorescence type.*—Numerous small bell-shaped flowers arranged on compound spikes on peduncles emerging from the base of the rosette.

*Inflorescence size.*—An average of 16.4 cm in height and 5.3 cm in width.

*Inflorescence number.*—An average of 75 in a 23-cm container.

*Flower fragrance.*—None.

*Flower quantity.*—Average of 60 flowers per flowering stem.

*Flower lastingness.*—Average of one week.

*Flower buds.*—Oblong to elliptic in shape, an average of 5 mm in diameter and 2 mm in diameter, 53C with tips 53A in color.

*Flower aspect.*—Outwards to drooping downwards.

*Flower type.*—Single, campanulate.

*Flower size.*—About 7 mm in length and 6 mm in diameter.

*Petals.*—About 5, rotate arrangement and implanted in the hypanthium at base, oblanceolate in shape, margin is entire, apex is acute, upper and lower surface is dull and glabrous, color of upper and lower surface when opening 65C, color of upper and lower surface when fully open 65A, an average of 4 mm in length and 1 mm in width.

*Calyx.*—Campanulate, sepals fused to hypanthium, 7 mm in length and 6 mm diameter.

*Sepals.*—An average of 5, fused into campanulate hypanthium, elliptic in shape, an average of 7 mm in length and 2 mm in width, margin is entire and fused into hypanthium, acute apex, fused base, color; immature upper and lower surface; 53C suffused with 53A towards the top, mature upper surface; 59D suffused with 59A towards the top and lower surface; 59C suffused with 59A towards the top, upper and lower surfaces are dull and densely covered with very short glandular hairs an average of 0.1 mm in length and matched to the sepals in color.

*Pedicels.*—An average of 2 mm in length and 0.5 mm in diameter, 183A in color, moderate strength, average angle of main flower pedicel 0° (0°=horizontal), average angle of secondary flower pedicels 30° to main pedicel.

Reproductive organs:

*Gynoecium.*—An average of 2 pistils, 4 mm in length, stigma; pointed in shape, 145D in color, style; an average of 3.5 mm in length and 145D in color, ovary; 150B in color.

*Androcoecium.*—An average of 5 stamens, anthers; ovate in shape, about 0.5 mm in length and 53A in color, filament; 2.5 mm in length and NN155C to NN155D in color, pollen; none detected.

*Seed/fruit.*—No fruit or seeds were observed.

It is claimed:

1. A new and distinct cultivar of *Heuchera* plant named 'Gauguin' as herein illustrated and described.

* * * * *